United States Patent [19]

Aldstadt, III

[11] Patent Number: 5,641,686
[45] Date of Patent: Jun. 24, 1997

[54] FLOW INJECTION TRACE GAS ANALYSIS METHOD FOR ON-SITE DETERMINATION OF ORGANOARSENICALS

[75] Inventor: Joseph H. Aldstadt, III, Orland Park, Ill.

[73] Assignee: The United States of America as represented by the United States Department of Energy, Washington, D.C.

[21] Appl. No.: 412,773

[22] Filed: Mar. 28, 1995

[51] Int. Cl.$^6$ .................................. G01N 27/26
[52] U.S. Cl. .................. 436/126; 436/52; 436/101; 422/82.01; 422/82.03; 422/82.04; 422/88; 422/98; 204/434
[58] Field of Search ............... 436/101, 52, 53, 436/126; 422/82.01, 82.03, 82.04, 88, 98; 204/434

[56] References Cited

U.S. PATENT DOCUMENTS

| | | |
|---|---|---|
| 3,966,412 | 6/1976 | Stroterhoff ................ 436/125 |
| 4,311,669 | 1/1982 | Spangler ................... 422/98 |
| 5,037,737 | 8/1991 | Liffmann et al. ........... 435/11 |
| 5,275,956 | 1/1994 | Bansho et al. ............. 436/125 |
| 5,292,423 | 3/1994 | Wang . | |

OTHER PUBLICATIONS

Zima et al. (AN 1994: 306883) HCA PLUS Abstract.
Greschonig, H. (AN 1993: 32161) HCA PLUS Abstract.
Kaplan, A. (AN 1978: 519660) HCA PLUS Abstract.
Andreae, M. (AN 1977:176989) HCA PLUS Abstract.

*Primary Examiner*—Long V. Le
*Attorney, Agent, or Firm*—Bradley W. Smith; Hugh W. Glenn; William R. Moser

[57] ABSTRACT

A method for real-time determination of the concentration of Lewisite in the ambient atmosphere, the method includes separating and collecting a Lewisite sample from the atmosphere in a collection chamber, converting the collected Lewisite to an arsenite ion solution sample, pumping the arsenite ion containing sample to an electrochemical detector connected to the collection chamber, and electrochemically detecting the converted arsenite ions in the sample, whereby the concentration of arsenite ions detected is proportional to the concentration of Lewisite in the atmosphere.

5 Claims, 2 Drawing Sheets

FLOW INJECTION TRACE GAS ANALYSIS METHOD FOR ON-SITE DETERMINATION OF ORGANOARSENICALS

CONTRACTUAL ORIGIN OF THE INVENTION

The United States Government has rights in this invention pursuant to Contract No. W-31-109-ENG-38 between the U.S. Department of Energy and The University of Chicago representing Argonne National Laboratory.

BACKGROUND OF THE INVENTION

This invention relates to a method and apparatus for determining the presence of volatile inorganic compounds in the environment. More specifically this invention relates to a method and apparatus for determining the presence and concentration of organoarsenicals, including Lewisite, in ambient air in near-real-time.

Lewisite collectively refers to Lewisite I, dichloro (2-chlorovinyl) arsine, $C_2H_2AsCl_3$, and its analogs Lewisite II, bis (2-chlorovinyl) chloroarsine, $(C_2H_2Cl)_2AsCl$, and Lewisite III, $(C_2H_2Cl)_3As$. Lewisite was developed during World War I as a chemical warfare agent. Several countries produced large quantities of the agent before, during and after World War II. The Chemical Weapons Convention treaty, recently signed, requires the destruction of Lewisite. In implementing the Chemical Weapons Convention treaty, it will be necessary to monitor the facilities at which various chemical agents including Lewisite may be stored for compliance with the agreement. The inspection procedures must meet stringent standards for safety, quality assurance and accountability. In preparing for these inspections a technology gap has been identified in the ability to detect and monitor for the presence of Lewisite in ambient air, particularly in the facilities where chemical warfare agents are stored.

Prior methods for monitoring the presence of trace levels of Lewisite in ambient air are based on sampling using liquid impingers or polymeric reactors and detection based on atomic absorption spectroscopy, ion chromatography, or gas chromatography. One of these prior methods uses the collection of Lewisite in a caustic-containing liquid impinger. The caustic solution in the impinger will decompose the Lewisite (using Lewisite I as an example) as shown in the following reaction mechanism:

$$C_2H_2AsCl_3 + 6OH^- \rightleftharpoons C_2H_2 + AsO_3^{3-} + 3Cl^- + 3H_2O$$

Acetylene that is produced when the Lewisite is decomposed by the hydroxide ion is measured by gas chromatography. This method is susceptible to interferences as well as the difficulty of quantitatively recovering the acteylene.

Two other methods, atomic absorption spectroscopy or ion chromatography, use this same type of sampling approach to measure the arsenite ion produced upon base hydrolysis. These methods require large and complex hardware and are thus suitable for the laboratory and are not portable so that they can be used at field sites.

Another prior method uses the reaction of Lewisite with 1,3-propanedithiol (or similar compounds) in a polymeric (e.g., polyester) reactor to convert Lewisite to a stable complex that can be analyzed by gas chromatography. However, this method is slow, insensitive, and imprecise.

SUMMARY OF THE INVENTION

Therefore in view of the above, it is an object of the present invention to provide an apparatus and method to measure trace levels of Lewisite in the ambient air which avoids the disadvantages of the prior art and provides additional structural and operating advantages.

An important feature of the invention is the provision of a Lewisite monitor, that continuously samples the atmosphere and is reproducible from sample to sample.

Another feature of the invention is the provision of an apparatus and method that can determine the presence and concentration of Lewisite down to the low to sub-parts per billion range within a ten minute time period.

A further feature of the invention is a provision of an apparatus and method as set forth capable of being employed in the field and which alerts inspectors or other personnel of the presence of Lewisite.

An additional feature of the invention is a provision of an apparatus as set forth that is small, compact, portable, suitcase-sized, and which has no installation requirements.

These and other features of the invention are attained by the provision of apparatus for determining the concentration of Lewisite in ambient atmosphere including mechanism for separating and collecting a Lewisite sample from the atmosphere, mechanism for converting the collected Lewisite to an arsenite ion solution sample, and mechanism for electrochemically detecting the converted arsenite ions in the sample, whereby the amount of arsenite ions detected is proportional to the concentration of Lewisite in the atmosphere.

DETAILED DESCRIPTION OF THE INVENTION

Figure 1:
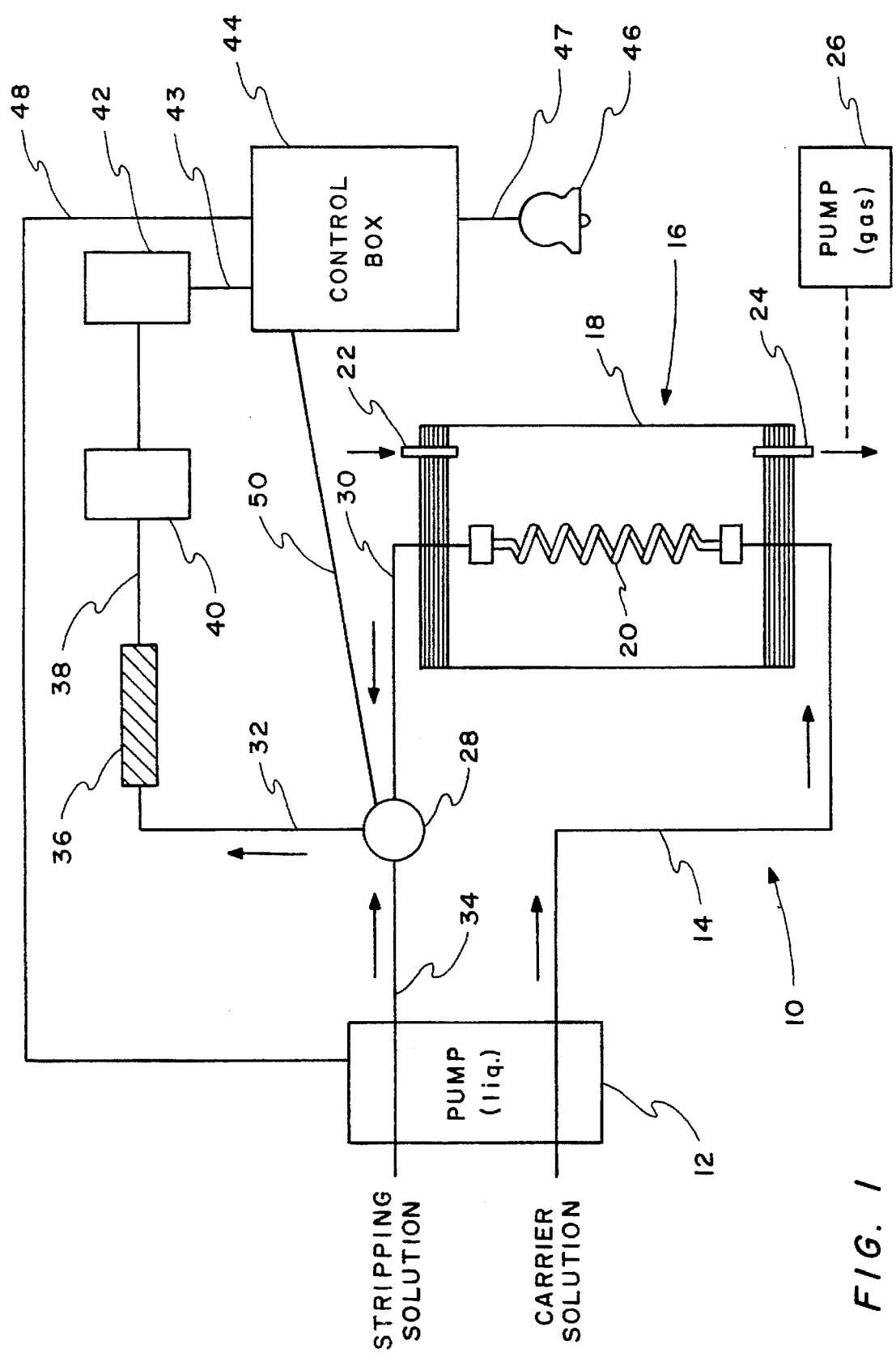
FIG. 1 is a schematic illustration of the apparatus used to determine the amount of Lewisite in ambient air.
Figure 2:
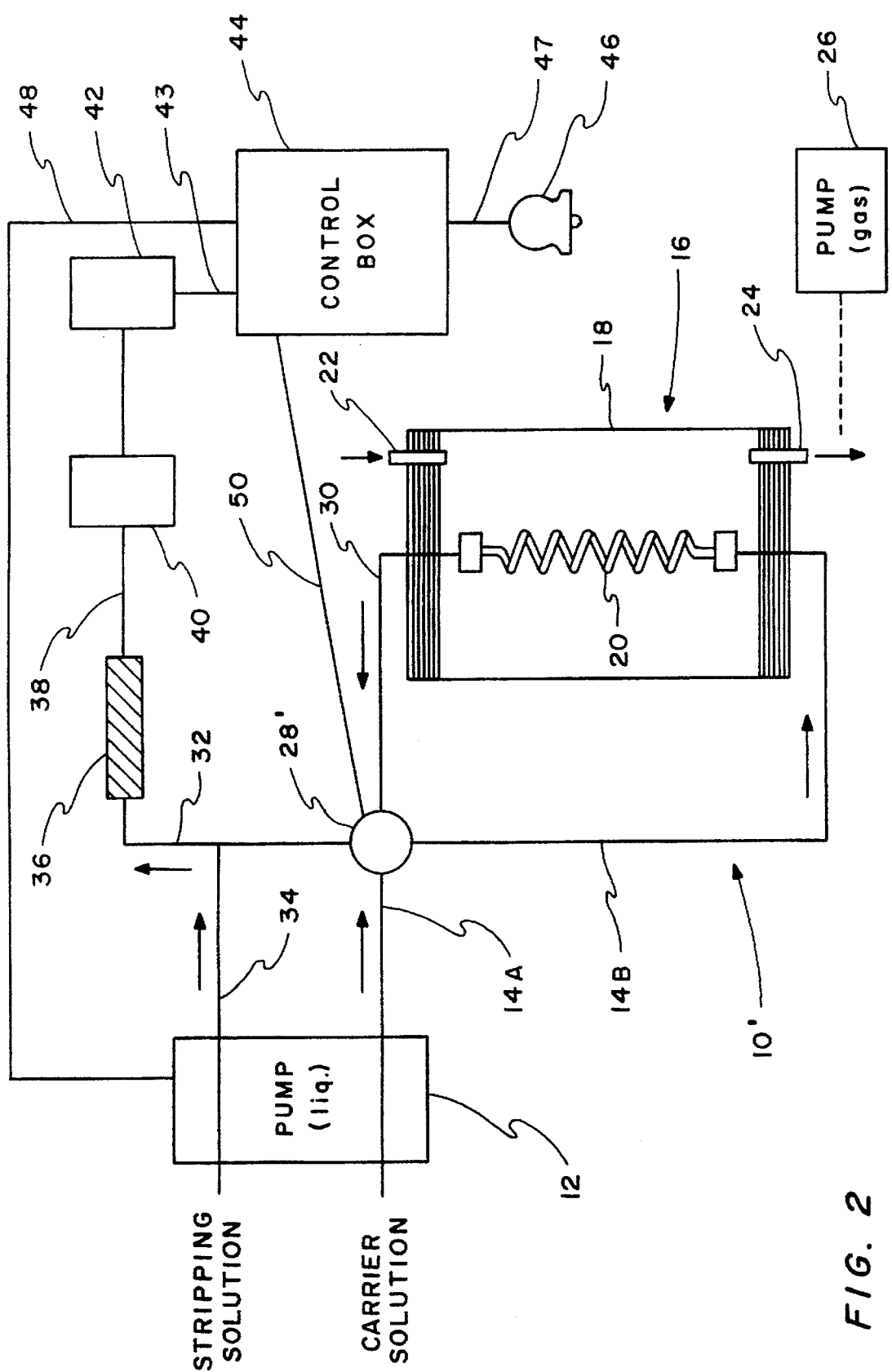
FIG. 2 is a schematic illustration of an alternative apparatus used to determine the amount of Lewisite in ambient air.

As discussed above, the term Lewisite refers to Lewisite I, Lewisite II and Lewisite III. For the sake of brevity, unless otherwise noted, only Lewisite I, dichloro (2-chlorovinyl) arsine will be discussed but the apparatus and method apply similarly to Lewisite I, II and III and combinations and mixtures thereof. As seen in FIG. 1, a trace gas analyzer 10 for determining organoarsenicals, like, dichloro (2-chlorovinyl) arsine, is schematically shown.

The analyzer includes a pump 12, preferably battery operated for passing a basic carrier solution, such as an aqueous potassium or sodium hydroxide solution at a pH between about 8 to 10, through narrow tubing 14 to a small gas permeation sampling unit 16.

The gas permeation sampling unit 16 includes an inert container 18, such as a 100 mL glass container. Within the container 18 is a permeation tube 20 which is connected to the tubing 14. The gas permeation sampling unit 16 also includes an ambient gas inlet 22 for drawing in ambient air from the room or site to be tested and a gas outlet 24. The gas outlet 24 is attached to a pump 26, which is preferably battery operated. The pump 26 controls the flow of ambient air that passes through the container 18 and contacts the permeation tube 20. If the air that is passed through the container 18 contains dichloro (2-chlorovinyl) arsine, a portion of the dichloro (2-chlorovinyl) arsine will pass or permeate into the permeation tube 20 which is made of a material, such as silicone rubber, which the dichloro (2-chlorovinyl) arsine is permeable to. The permeation tube 20, rather than being a straight tube, is also preferably coiled to provide a large amount of permeable surface area in relatively small space for the air that passes through the container 18 to contact. A useful tube is a coiled silicone rubber tube having dimensions of 1.6 mm outside diameter× 0.8 mm inside diameter×60 cm long. The permeation tube 20 allows only certain materials to permeate into its interior and thereby separates the dichloro (2-chlorovinyl) arsine from most of the other components found in atmospheric air.

Once the dichloro (2-chlorovinyl) arsine passes through the permeation tube 20, it will contact the basic solution which is contained in the interior of the permeation tube 20 and which was fed through tubing 14 into the permeation tube 20. The dichloro (2-chlorovinyl) arsine will dissolve in the basic solution and be base hydrolyzed to arsenite ions according to the following reaction mechanism:

$$C_2H_2AsCl_3 + 6OH^- \rightleftharpoons AsO_3^{3-} + C_2H_2 + 3Cl^- + 3H_2O$$

(Lewisite II and Lewisite III are similarly base hydrolyzed to also form one arsenite ion per Lewisite molecule base hydrolyzed.)

After the permeation tube 20 has been contacted for a given amount of time with a given amount of atmospheric air, a two position valve 28 is properly positioned and the basic solution now containing arsenite ions, in the $AsO_3^{3-}$ form, is pumped out of the permeation tube 20 and a sample plug moves through the narrow tubing 30, through valve 28 into narrow tubing 32 where it contacts, if necessary and depending, as discussed below, on the detector utilized, an acidic stripping solution that is pumped by pump 12 through narrow tubing 34, valve 28 into the tubing 32 where it contacts the basic solution. The stripping solution is preferably a nonoxidizing, strong acid, such as hydrochloric acid. The stripping solution forms a solution in tubing 32 with the basic carrier solution coming from the permeation tube 20 that has a pH lower than the basic carrier solution. A lower pH solution, as described below, is necessary for some electrochemical detectors. The solution having a reduced pH in tubing 32 passes through a mixing coil 36 which thoroughly mixes the solution. The mixing coil can simply be a tube wrapped around a rod.

After the solution has been thoroughly mixed, it passes via narrow tubing 38 into flow cell 40, such as a wall-jet flow cell, where the concentration of arsenite ions is electrochemically detected by a suitable electrochemical detector having electrodes in the flow cell 40 which are connected to a potentiostat 42. If the detector is, preferably, a potentiometric stripping analyzer which performs potentiometric stripping analysis, the combined solution preferably has a pH less than 1 to allow the chemical reactions for detecting arsenite ions necessary for proper operation of the detector to take place. The stripping solution consists of a nonoxidizing acid to prevent the arsenite ions from oxidizing to arsenate ions, $AsO_4^{3-}$, which will not be detected by the detector. If arsenate ions are generated, an artificially low arsenite ion concentration would be detected.

The concentration of arsenite ions detected in the flow cell 40, as discussed below, is proportional to the concentration of dichloro (2-chlorovinyl) arsine in the air. The detector is, preferably, electrically connected via electrical lead 43 to a control box 44, such as an instrument control and data acquisition computer, which determines the concentration of arsenite ion detected and sets off a warning alarm 46 electrically connected via electrical lead 47 to the control box 44 if the concentration of arsenite ions detected exceeds a predetermined threshold limit proportional to a given concentration of dichloro (2-chlorovinyl) arsine in the ambient air.

By way of example and without limitation, the detector performs potentiometric stripping analysis generally in two steps as follows. Arsenite ion, for simplicity represented as $As^{3+}$, is first preconcentrated by being reduced (i.e., gaining electrons) onto a suitable electrode including a (gold electrode or glassy carbon electrode covered with a thin gold film) disposed in the flow cell 40. This step is usually called the "deposition step" or the "plating step", and is expected to last several minutes and is illustrated by the following reduction reaction.

$$As^{3+} + 3e^- + Au \rightleftharpoons (AsAu)$$

During this process, the electrode is held at a constant voltage (i.e., constant potential). This potential provides electrons with sufficient energy to reduce the $As^{3+}$ ion to the (AsAu) complex. For example, the potential where the above reaction occurs is about +150 mV (measured versus a saturated calomel reference electrode in about one molar HCl). Therefore, during the deposition step the gold electrode is held at a potential more negative than that value (e.g., −100 mV) to be sure that there will be energetic electrons to cause the above reaction to occur readily. The longer the deposition step lasts, the more arsenic can be complexed and the lower the concentration level of arsenite in the flow cell 40 can be determined.

The second step is known as the "stripping step". During this step, the analytical signal is measured. The arsenic metal that was plated onto the gold electrode during the deposition step is stripped from the electrode's surface. In this example, that would occur around +150 mV, where the oxidation reaction $$(AsAu) \rightleftharpoons As^{3+} + 3e^- + Au$$

occurs.

The stripping of the metal off the electrode is done by disconnecting the applied potential and using the electrode to oxidize the arsenite. A constant current (low μA range) is passed through the electrode to cause the oxidation reaction. The potential is disconnected to allow it to change from the negative value (e.g., starting at the −100 mV used during the deposition step) to a preset positive value (e.g., +500 mV, where the gold electrode itself begins to oxidize). As the potential changes through this range, it will pass through the $As/As^{3+}$ redox potential (~150 mV). At this point, the electrode acts as an oxidant and arsenite ion is stripped from the electrode. Because of the arsenic metal present (as the AsAu plated species), the rate of change of the potential with time will decrease as it passes through this potential. As the arsenic strips out, a peak will register, in a plot of $\Delta t/\Delta E$ vs. E, where E stands for potential and t stands for time, on a plot created by the potentiostat. A useful potentiostat is a Radiometer PSU 22 TraceLab™ potentiostat. The area under the peak is directly proportional to the concentration of the arsenite ion in the solution in the flow cell and dichloro (2-chlorovinyl) arsine in the ambient air. Potentiometric stripping analysis is more fully described in "Potentiometric Stripping Analysis," by Daniel Jagner as published in *The Analyst*, Vol. 107, No. 1275 (June 1982) and in "Trace Element Analysis by Computerized Stripping Potentiometry," by Anne Margrethe Graabæk and Bjørn Jeberg, as published in *American Laboratory*, Vol. 25, Issue 8, 1993, which are both incorporated herein by reference.

The trace gas analyzer 10 is preferably calibrated to correlate the concentration of arsenite ions in the flow cell 40 to the concentration of dichloro (2-chlorovinyl) arsine in air by pumping carrier solution into the permeation tube 20, shutting the pump 12 off for a predetermined period of time, passing a dilute dichloro (2-chlorovinyl) arsine gas solution of known concentration through the gas permeation sampling unit 16 to permeate the permeation tube 20 at a predetermined and known volumetric rate.

The volumetric rate and the time the pump 12 is turned off can be determined and/or adjusted to meet the sensitivity demands of the detector and the target concentration of dichloro (2-chlorovinyl) arsine in ambient air. If the volumetric rate is increased and the residence time the basic solution is maintained in the permeation tube 20 is a longer period of time, more dichloro (2-chlorovinyl) arsine molecules have an opportunity to permeate through the permeation tube 20 to be base hydrolyzed into arsenite ions capable of detection. The longer the residence time of the basic solution in the permeation tube 20 (i.e., the time the pump 12 is shut off) and the greater the volumetric rate of gas passage through the gas permeation sampling unit 16, the more concentrated the arsenite ion containing solution in the permeation tube 20 can become. This is very important because dichloro (2-chlorovinyl) arsine needs to be detected at concentrations less than 0.003 $mg/m^3$ or 3 parts per trillion by volume, the applicable U.S. military eight hour time weighted average (TWA) concentration. Since all the dichloro (2-chlorovinyl) arsine that passes through the gas permeation sampling unit 16 does not permeate into the permeation tube 20 and become converted to arsenite ions and because it is believed that potentiometric stripping analysis detectors can only measure arsenite ion concentrations down to about 0.1 parts per billion, the arsenite ion solution in the permeation tube 20 must be concentrated to enable the detector to be able to detect the low levels of dichloro (2-chlorovinyl) arsine found in the atmosphere.

After the calibration gas has been passed through the gas permeation sampling unit 16 at the predetermined volumetric rate and the pump 12 has been turned off for the predetermined time, the pump 12 is started and the arsenite ion containing sample plug is pumped out the permeation tube 20 to the flow cell 40 and the concentration of arsenite ions are detected as previously described. If necessary, additional dichloro (2-chlorovinyl) arsine calibration gases of different known concentrations are similarly sampled. A calibration curve is generated by the control means 10 and samples from the atmospheric air are compared to the calibration curve to determine the amount of dichloro (2-chlorovinyl) arsine in the air.

In addition to using dichloro (2-chlorovinyl) arsine calibration gases, the trace gas analyzer 10 may use other dichloro (2-chlorovinyl) arsine simulated standards which have been previously correlated to the actual dichloro (2-chlorovinyl) arsine calibration gases to calibrate the trace gas analyzer 10. This correlation includes taking into account the flow rate of the calibration gases through the gas permeation sampling unit 16, the differences between the standard's and the actual calibration gases' permeability to the permeation tube 20, the flow rate of the calibration gas and the rate of base hydrolysis. It is believed that a useful simulated standard may include a dilute liquid solution of (much less toxic) $AsCl_3$ or a vapor generated gas solution of $AsCl_3$.

In addition to measuring single samples of dichloro (2-chlorovinyl) arsine in the air, the trace gas analyzer 10 can continuously operate to sequentially sample the ambient air. This is accomplished by using a flow injection analysis technique. Flow injection analysis is more fully discussed in the book authored by J. Ruzicka and E. H. Hansen, entitled *Flow Injection Analysis*, (John Wiley & Sons, 2nd Edition, 1988) and is incorporated herein by reference. This technique is characterized in that the trace gas analyzer 10 sequentially processes each sample in exactly the same way, through the analyzer. In other words, what happens to one sample happens in exactly the same way to any other sample. This technique is therefore reliable and reproducible from sample to sample. Further, the trace gas analyzer 10 allows two dichloro (2-chlorovinyl) arsine samples to be at various stages of analysis within the trace gas analyzer 10 at the same time.

In order for continuous sequential air sampling to occur, the control box 44 is connected to the pump 12 and valve 28 by electrical leads 48 and 50, respectively. The operation occurs as follows: Gas pump 26 is turned on and continuously operates. Control box 44 turns the pump 12 on and the basic carrier solution is pumped into the permeation tube 20. The control box 44 turns the pump 12 off for the predetermined time, as discussed above to obtain the first sample plug. Dichloro (2-chlorovinyl) arsine permeates the permeation tube 20 and dissolves into the liquid carrier where it is rapidly and quantitatively base hydrolyzed to arsenite ion. The control box 44 turns the liquid pump 12 back on and moves valve 28 to a proper position, and the first sample plug is pumped out of the permeation tube 20 toward the flow cell 40. On the way, it is combined with an acidic stripping solution stream valve 28 to neutralize the basic solution so that the arsenite ion will be in a form (low pH solution) required for the potentiometer stripping analysis detection method. When the sample plug reaches the flow cell 40, the control box 44 stops the pump 12 (for the same predetermined amount of time pump 12 is shut off and necessary for dichloro (2-chlorovinyl) arsine to permeate the permeation tube 20) and changes the position of valve 28 to prevent the acid solution from continuing to combine with the base solution. At this point, the potentiometer stripping analysis electrochemical detection measurement is made. Simultaneously, the next sample plug is being gathered in the permeation tube 20. The peak (if any) from the potentiometer stripping analysis measurement is integrated and the result is compared to a threshold. If it exceeds the threshold, the control box 44 sounds the alarm. The control box 44 turns the pump 12 back on and changes the position of valve 28, and the next sample plug is pumped toward the flow cell 40 and a new sample plug is prepared in the gas permeation sampling unit 16. It is believed that the ambient air can be sampled at least as often as every ten minutes with the trace gas analyzer 10.

In an alternative embodiment, as seen in FIG. 2, in which like parts are numbered the same for brevity, a trace gas analyzer 10' is provided which is the same as the embodiment shown in FIG. 1, except that line 34 carrying the stripping solution from pump 12 is directly connected to line 32 and a two position valve 28' is connected to tubing 14A and 14B to be disposed between the pump 12 and the permeation tube 20. This embodiment allows the valve 28' to now control both the sample plug exiting the permeation tube 20 to be sent to the flow cell 40 as well as the basic carrier solution entering the permeation tube 20.

While there has been disclosed what is considered to be the preferred embodiment of the present invention, it is understood that various changes in the details may be made without departing from the spirit, or sacrificing any of the advantages of the present invention.

The embodiments of the invention in which an exclusive property or privilege is claimed are defined as follows:

1. A method for real-time determination of the concentration of Lewisite in ambient atmosphere comprising the steps of:

providing a permeation tube having an interior;

separating and collecting a Lewisite sample from the atmosphere by passing atmospheric air about the permeation tube, whereby the Lewisite permeates into the interior of the tube;

concentrating the Lewisite in the sample during collection;

converting the collected Lewisite to an arsenite ion containing solution sample;

pumping the arsenite ion containing solution sample to an electrochemical detector connected to the permeation tube; and electrochemically detecting the converted arsenite ions, whereby the concentration of the arsenite ions detected is proportional to the concentration of Lewisite in the atmosphere.

2. The method of claim 1, wherein the Lewisite is converted to arsenite ions by base hydrolysis.

3. The method of claim 1, further including passing a basic solution through the interior of the permeation tube to contact the Lewisite which has permeated into the interior.

4. The method of claim 3, further including lowering the pH of the arsenite ion containing solution to less than about 1 and wherein the electrochemical detection of the converted arsenite ions includes potentiometric stripping analysis of the arsenite ion containing solution sample.

5. The method of claim 1 further comprising comparing the concentration of electrochemically detected arsenite ions to a threshold value and sounding an alarm if the threshold value is exceeded.

* * * * *